US011158417B1

(12) United States Patent
Neumann

(10) Patent No.: US 11,158,417 B1
(45) Date of Patent: Oct. 26, 2021

(54) SYSTEM AND METHOD FOR GENERATING A DIGESTIVE DISEASE NOURISHMENT PROGRAM

(71) Applicant: KPN INNOVATIONS, LLC., Lakewood, CO (US)

(72) Inventor: Kenneth Neumann, Lakewood, CO (US)

(73) Assignee: KPN INNOVATIONS, LLC., Lakewood, CO (US)

(*) Notice: Subject to any disclaimer, the term of this patent is extended or adjusted under 35 U.S.C. 154(b) by 0 days.

(21) Appl. No.: 17/136,109

(22) Filed: Dec. 29, 2020

(51) Int. Cl.
  *G16H 20/60* (2018.01)
  *G16H 10/60* (2018.01)
  *G16H 50/30* (2018.01)
  *G16H 50/70* (2018.01)
  *G16H 50/20* (2018.01)
  *G06N 20/00* (2019.01)
  (Continued)

(52) U.S. Cl.
  CPC ............ *G16H 20/60* (2018.01); *G06N 20/00* (2019.01); *G16H 10/40* (2018.01); *G16H 10/60* (2018.01); *G16H 50/20* (2018.01); *G16H 50/30* (2018.01); *G16H 50/70* (2018.01); *A61B 5/42* (2013.01); *A61B 5/4833* (2013.01)

(58) Field of Classification Search
  CPC ... G06F 1/00–2221/2153; G16H 10/00–80/00; G06N 3/00–99/007
  See application file for complete search history.

(56) References Cited

U.S. PATENT DOCUMENTS 8,560,334 B2 * 10/2013 Lahteenmaki ......... G16H 20/60
                                                                705/2
10,325,685 B2    6/2019 Apte
10,360,346 B2    7/2019 Apte
(Continued)

FOREIGN PATENT DOCUMENTS

CN   108766526 A  * 11/2018  ............. G16H 20/60
KR   102011249 B1 *  8/2019  ............. G06Q 30/02
WO   2019018580      1/2019

OTHER PUBLICATIONS

Enam et al., "Prebiotics: tools to manipulate the gut microbiome and metabolome," Journal of Industrial Mircobiology and Biotechnology: vol. 45, pp. 1445-1459. (Year: 2019).*

(Continued)

*Primary Examiner* — Elaine Gort
*Assistant Examiner* — Jonathon A. Szumny
(74) *Attorney, Agent, or Firm* — Caldwell Intellectual Property Law, LLC

(57) ABSTRACT

A system for generating a digestive disease nourishment program includes a computing device configured to receive a digestive biomarker relating to a user, generate a digestive parameter as a function of the digestive disease biomarker, determine a digestive profile as a function of the digestive parameter. The computing system is configured to identify a nutrition element as a function of the digestive profile, wherein identifying includes determining, for each nutrition element, a nourishment score as a function of the effect of the nutrition element on the digestive profile and identifying the nutrition element as a function of the nourishment score. The system configured to generate a digestive disease nourishment program as a function of the nutrition element and the digestive profile.

16 Claims, 7 Drawing Sheets

(51) Int. Cl.
*G16H 10/40* (2018.01)
*A61B 5/00* (2006.01)

(56) References Cited

U.S. PATENT DOCUMENTS

| | | | | |
|---|---|---|---|---|
| 10,553,316 | B1 | 2/2020 | Neumann | |
| 10,553,319 | B1 | 2/2020 | Neumann | |
| 2011/0009708 | A1* | 1/2011 | Boyes | G16H 20/60 600/300 |
| 2011/0054928 | A1* | 3/2011 | Sullivan | G16H 20/60 705/2 |
| 2013/0004923 | A1* | 1/2013 | Utter, II | A61B 5/7465 434/127 |
| 2014/0088995 | A1* | 3/2014 | Damani | G06Q 10/10 705/2 |
| 2014/0119996 | A1* | 5/2014 | Horning | A23L 33/30 422/82.01 |
| 2014/0287384 | A1* | 9/2014 | Boyes | G09B 5/02 434/127 |
| 2015/0317453 | A1* | 11/2015 | Cunningham | B65D 83/0409 700/232 |
| 2016/0198996 | A1* | 7/2016 | Dullen | A61B 5/02055 600/301 |
| 2017/0202802 | A1* | 7/2017 | Fernandez | A61K 31/4415 |
| 2017/0249445 | A1* | 8/2017 | Devries | G16H 20/60 |
| 2017/0321256 | A1* | 11/2017 | Fricke | G16B 40/20 |
| 2018/0039759 | A1* | 2/2018 | Astigarraga | G16H 20/60 |
| 2018/0240542 | A1* | 8/2018 | Grimmer | A61P 25/18 |
| 2018/0308390 | A1* | 10/2018 | Moser | A63B 24/0006 |
| 2018/0363031 | A1* | 12/2018 | Becares | G16B 40/00 |
| 2018/0374385 | A1* | 12/2018 | Benefield | A63B 24/0062 |
| 2019/0027060 | A1* | 1/2019 | Ishii | G06Q 30/02 |
| 2019/0050534 | A1 | 2/2019 | Apte | |
| 2019/0079073 | A1* | 3/2019 | Hyde | G01N 33/5038 |
| 2019/0145988 | A1* | 5/2019 | Haddad | G16H 20/60 514/52 |
| 2019/0252058 | A1* | 8/2019 | Wolf | G16H 20/60 |
| 2019/0290172 | A1* | 9/2019 | Hadad | A61B 5/14532 |
| 2019/0295440 | A1* | 9/2019 | Hadad | G06F 40/216 |
| 2020/0066181 | A1* | 2/2020 | Hadjigeorgiou | G16H 20/60 |
| 2020/0194106 | A1* | 6/2020 | Olson | G16H 40/67 |
| 2020/0219605 | A1* | 7/2020 | Govindjee | G16H 40/67 |
| 2020/0320132 | A1 | 10/2020 | Neumann | |
| 2020/0342353 | A1 | 10/2020 | Neumann | |
| 2020/0380458 | A1 | 12/2020 | Neumann | |
| 2021/0065873 | A1* | 3/2021 | Wolf | G16H 20/60 |

OTHER PUBLICATIONS

"Prebiotics & Probiotics," capture of https://badgut.org/information-centre/a-z-digestive-topics/prebiotics-probiotics/ from Sep. 29, 2020 Gastrointestinal Society—Canadian Society of Intestinal Research (Year: 2020).*

Makki et al., "The Impact of Dietary Fiber on Gut Microbiota in Host Health and Disease," Cell Host & Microbe, vol. 23, pp. 705-715 (Year: 2018).*

Tran et al., "An overview of recommender system in the healthy food domain," J Intell Inf Syst (2018) 50:501-526. (Year: 2018).*

Crohn's & Colitis 360 • vol. 2, No. 4, Oct. 2020; doi: 10.1093/crocol/otaa087; Title: Precision Nutrition Initiative: Toward Personalized Diet Recommendations for Patients With Inflammatory Bowel Diseases; Date: Oct. 2020; By: Hurtado, Lorentzo.

Nature Reviews Microbiology vol. 17, pp. 742-753(2019); https://doi.org/10.1038/s41579-019-0256-8; Title: Diet—microbiota interactions and personalized nutrition; Date: Sep. 20, 2019; By: Kolodziejczyk.

J. Clin. Med. 2020, 9, 125; doi:10.3390/jcm9010125; Title: Effectiveness of Two Dietary Approaches on the Quality of Life and Gastrointestinal Symptoms of Individuals with Irritable Bowel Syndrome; by: Guerriero; Date: Nov. 11, 2019.

Current Clinical Pharmacology, 2018, 13, 1-9 DOI: 10.2174/1574884713666180807143606; Title: Therapeutic approach for irritable bowel syndrome: old and new strategies; By: Usau-Satta; Date: Mar. 4, 2018.

Nutrients 2020, 12(11), 3368; https://doi.org/10.3390/nu12113368; Title: Low Fermentable Oligo-Di-and Mono-Saccharides and Polyols (FODMAPs) or Gluten Free Diet: What Is Best for Irritable Bowel Syndrome?; By: Bellini; Date: Sep. 16, 2020.

The American Journal of Clinical Nutrition, vol. 96, Issue 6, Dec. 2012, pp. 1346-1353, https://doi.org/10.3945/ajcn.111.018838; Title: Individualized nutrition intervention is of major benefit to colorectal cancer patients: long-term follow-up of a randomized controlled trial of nutritional therapy.; by: Ravasco; Date: 2012.

Proc. ACM Interact. Mob. Wearable Ubiquitous Technol. vol. 3, No. 1, Article 7. Publication date: Mar. 2019.; DOI: http://dx.doi.org/10.1145/3314394; Title: Identifying and Planning for Individualized Change: Patient-Provider Collaboration Using Lightweight Food Diaries in Healthy Eating and Irritable Bowel Syndrome; Date: Mar. 2019; By: Chung.

* cited by examiner

SYSTEM AND METHOD FOR GENERATING A DIGESTIVE DISEASE NOURISHMENT PROGRAM

FIELD OF THE INVENTION

The present invention generally relates to the field of artificial intelligence. In particular, the present invention is directed to methods and systems for generating a digestive disease nourishment program.

BACKGROUND

Current nourishment program generation systems do not account for digestive characteristics of an individual. This leads to inefficiency of a nourishment program generation system and a poor nutrition program for the individual. This is further complicated by a lack of uniformity of nutritional programs, which results in dissatisfaction of individuals.

SUMMARY OF THE DISCLOSURE

In an aspect, a system for generating a digestive disease nourishment program includes a computing device configured to receive at least a digestive biomarker relating to a user, generate at least a digestive parameter of a plurality of digestive parameters as a function of the digestive disease biomarker and determine a digestive profile as a function of the at least a digestive parameter. The computing system is configured to identify at least a nutrition element as a function of the digestive profile, wherein identifying includes determining, for each nutrition element of a plurality of nutrition elements, a nourishment score as a function of the effect of the nutrition element on the digestive profile and identifying the nutrition element as a function of the nourishment score. The system configured to generate a digestive disease nourishment program as a function of the nutrition element and the digestive profile.

In another aspect, a method for generating a digestive disease nourishment program includes receiving at least a digestive biomarker relating to a user, generating at least a digestive parameter of a plurality of digestive parameters as a function of the digestive disease biomarker, and determining a digestive profile as a function of the at least a digestive parameter. Method includes identifying at least a nutrition element as a function of the digestive profile, wherein identifying includes determining, for each nutrition element of a plurality of nutrition elements, a nourishment score as a function of the effect of the nutrition element on the digestive profile, identifying at least a nutrition element as a function of the nourishment score, and generating a digestive disease nourishment program as a function of the nutrition element and the digestive profile.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for generating a digestive disease nourishment program. System for generating a digestive disease nourishment program includes a computing device configured to receive at least a digestive biomarker relating to a user, generate at least a digestive parameter of a plurality of digestive parameters as a function of the digestive disease biomarker, and determine a digestive profile as a function of the at least a digestive parameter. The digestive profile includes a quantitative digestive health score correlated to the at least a digestive parameter and the digestive profile includes an absorption condition correlated to the at least a digestive parameter. The computing system is configured to identify at least a nutrition element as a function of the digestive profile, wherein identifying includes determining, for each nutrition element of a plurality of nutrition elements, a nourishment score as a function of the effect of the nutrition element on the digestive profile and identifying the nutrition element as a function of the nourishment score. The system configured to generate a digestive disease nourishment program as a function of the nutrition element and the digestive profile.

Figure 1:
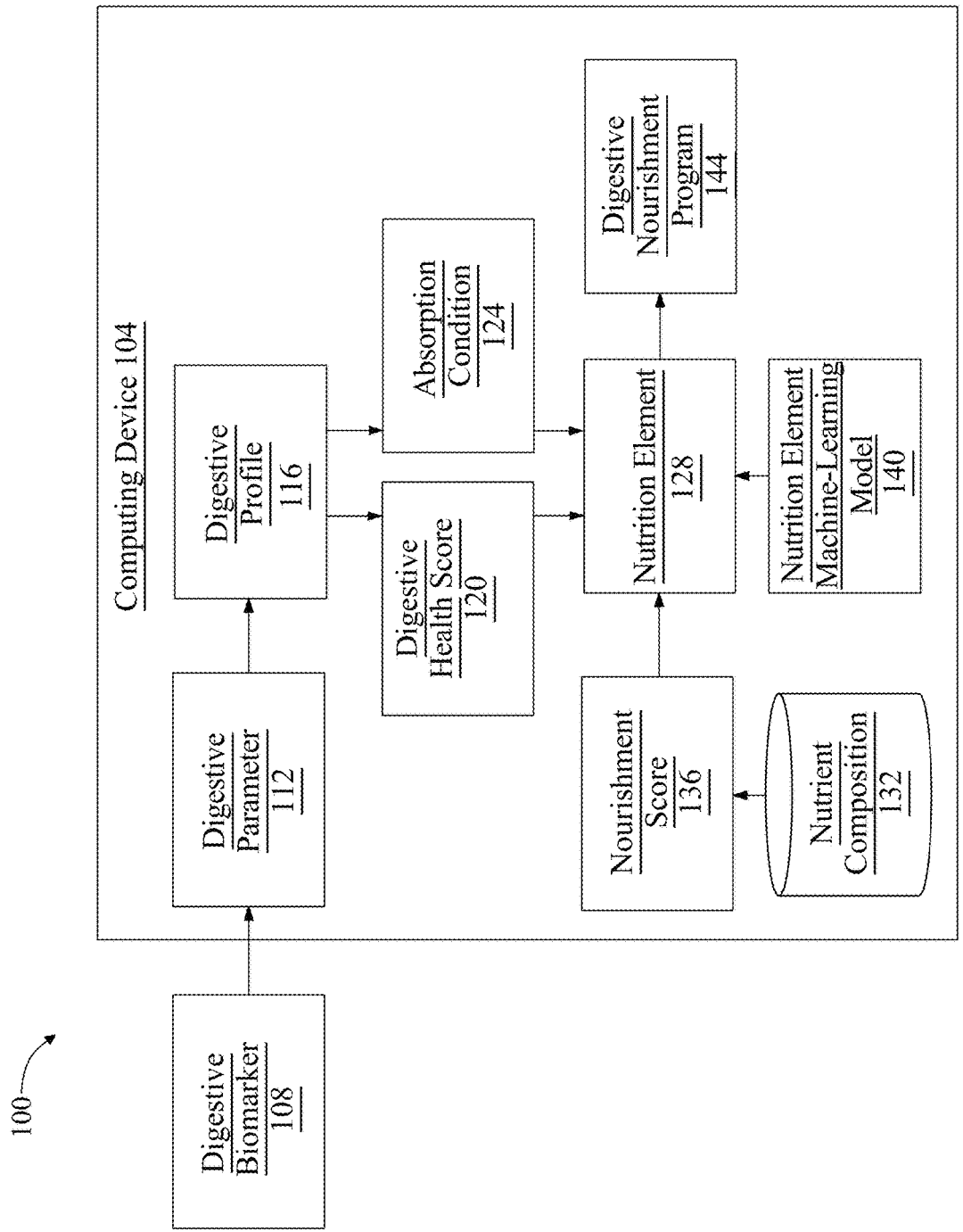
FIG. 1 is a block diagram illustrating an exemplary embodiment of a system for generating a digestive disease nourishment program.

Referring now to FIG. 1, an exemplary embodiment of a system 100 for generating a digestive disease nourishment program is illustrated. System 100 includes a computing device 104. Computing device 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, a system 100 for generating a digestive disease nourishment program, the system including a computing device 104, the computing device 104 configured to receive at least a digestive biomarker 108 relating to a user. A "digestive biomarker," for the purposes of this disclosure, is an element submitted to the system by a user relating to a digestive disease state relating to the user. Digestive biomarker 108 may include result of one or more tests relating to the user. Tests relating to a user may include blood panel, stool sample, urine sample, blood sample, colorectal transit study, defecography, lower gastrointestinal (GI) series, upper gastrointestinal (GI) series, barium enema, magnetic resonance imaging (MM), magnetic resonance cholangiopancreatography (MRCP), oropharyngeal motility (swallowing) study, stool culture, fecal occult blood test, barium beefsteak meal, computed tomography (CT) scan, radioisotope gastric-emptying scan, ultrasound, colonoscopy, esophagogastroduodenoscopy (also called EGD or upper endoscopy), sigmoidoscopy, and anorectal manometry. Receiving at least a digestive biomarker 108 includes receiving a prior diagnosis of a digestive disease relating to the user. A "prior diagnosis", for the purposes of this disclosure, is a prior digestive disease state relating to a user, wherein the user has been diagnosed with a digestive disease or condition. Prior diagnosis of a digestive disease may include prior diagnosis of Barrett esophagus, Collagenous colitis, Crohn's disease, Lynch syndrome, Gallstones, Ulcerative colitis, Celiac disease, Crohn's disease, Irritable bowel syndrome, Diverticulitis, Gastroesophageal reflux disease, 22q11.2 deletion syndrome, Aagenaes syndrome, Abetalipoproteinemia, Accessory pancreas, Achalasia microcephaly syndrome, Acrodermatitis enteropathica, Acute fatty liver of pregnancy, Adult polyglucosan body disease, Agenesis of the dorsal pancreas, Al-Gazali-Donnai-Mueller syndrome, ALG13-CDG, ALG2-CDG (CDG-Ii), ALG6-CDG (CDG-Ic), ALG8-CDG (CDG-Ih), ALG9-CDG (CDG-IL), Alpers syndrome, Alpha-1 antitrypsin deficiency, Ankyloblepharon filiforme imperforate anus, Annular pancreas, Aplasia cutis congenita intestinal lymphangiectasia, Arterial tortuosity syndrome, Arthrogryposis renal dysfunction cholestasis syndrome, Arts syndrome, Atresia of small intestine, Autoimmune gastrointestinal dysmotility, Autoimmune hepatitis, Autoimmune lymphoproliferative syndrome due to CTLA4 haploinsufficency, Autosomal recessive early-onset inflammatory bowel disease, Axenfeld-Rieger syndrome, B4GALT1-CDG (CDG-IId), Baller-Gerold syndrome, Bannayan-Riley-Ruvalcaba syndrome, Bantu siderosis, Bardet-Biedl syndrome, Bardet-Biedl syndrome 1, Bardet-Biedl syndrome 10, Bardet-Biedl syndrome 11, Bardet-Biedl syndrome 12, Bardet-Biedl syndrome 2, Bare lymphocyte syndrome 2, Benign recurrent intrahepatic cholestasis 1, Benign recurrent intrahepatic cholestasis 2, Bifid nose with or without anorectal and renal anomalies, Bile duct cancer, Biliary atresia, Boerhaave syndrome, Budd-Chiari syndrome, Cantu syndrome, Caroli disease, Cat eye syndrome, Caudal regression sequence, Cerebrotendinous xanthomatosis, Childhood hepatocellular carcinoma, Cholesteryl ester storage disease, Chronic granulomatous disease, Chronic hiccups, Chylomicron retention disease, Chylous ascites, Citrullinemia type II, Classical-like Ehlers-Danlos syndrome, COACH syndrome, COG4-CDG (CDG-IID, Collagenous gastritis, Congenital bile acid synthesis defect, type 1, Congenital bile acid synthesis defect, type 2, Congenital chloride diarrhea, Congenital diaphragmatic hernia, Congenital disorders of glycosylation, Congenital lactase deficiency, Congenital sucrase-isomaltase deficiency, Cornelia de Lange syndrome, Cowden syndrome, Crigler Najjar syndrome, type 1, Crigler-Najjar syndrome type 2, Cronkhite-Canada disease, Currarino triad, Cutaneous photosensitivity and colitis, lethal, Cutis laxa, autosomal dominant, Cutis laxa, autosomal recessive type 1, Cystic fibrosis, Dandy-Walker cyst with Renal-Hepatic-Pancreatic dysplasia, DDOST-CDG (CDG-Ir), Deafness, dystonia, and cerebral hypomyelination, Desmoplastic small round cell tumor, Disseminated peritoneal leiomyomatosis, Donnai-Barrow syndrome, DPM2-CDG, Dubin-Johnson syndrome, Duodenal atresia, Duodenal ulcer due to antral G-cell hyperfunction, Emanuel syndrome, Eosinophilic gastroenteritis, Esophageal atresia, Exstrophy of the bladder, Familial caudal dysgenesis, Familial pancreatic cancer, Familial visceral myopathy with external ophthalmoplegia, Fanconi Bickel syndrome, Feingold syndrome, Fraser syndrome, Froster-Huch syndrome, Fryns syndrome, Galactokinase deficiency, Galactose epimerase deficiency, Gardner syndrome, Gastrocutaneous syndrome, Gastrointestinal Stromal Tumors, Gastroschisis, Geroderma osteodysplastica, Glucose-galactose malabsorption, Glycogen storage disease type 1A, Glycogen storage disease type 1B, Glycogen storage disease type 3, Glycogen storage disease type 6, Goblet cell carcinoid, Goldberg-Shprintzen megacolon syndrome, GRACILE syndrome, Hemochromatosis type 2, Hemochromatosis type 3, Hemochromatosis type 4, Hepatic encephalopathy, Hepatic veno-occlusive disease, Hepatic venoocclusive disease with immunodeficiency, Hepatoblastoma, Hereditary diffuse gastric cancer, Hereditary folate malabsorption, Hereditary fructose intolerance, Hereditary hemorrhagic telangiectasia, Hereditary hemorrhagic telangiectasia type 2, Hereditary hemorrhagic telangiectasia type 3, Hereditary hemorrhagic telangiectasia type 4, Hereditary pancreatitis, Hirschsprung disease, Hirschsprung disease type d brachydactyly, Hyperbilirubinemia transient familial neonatal, Ichthyosis, leukocyte vacuoles, alopecia, and sclerosing cholangitis, Idiopathic achalasia, Imerslund-Grasbeck syndrome, Immunodysregulation, polyendocrinopathy and enteropathy X-linked, Infantile liver failure syndrome 1, Infantile onset spinocerebellar ataxia, Intestinal atresia multiple, Intrahepatic cholestasis of pregnancy, Jejunal atresia, Johanson-Blizzard syndrome, Juvenile polyposis syndrome, Kabuki syndrome, Kernicterus, Klatskin tumor, Limb-body wall complex, LRBA deficiency, Lucey-Driscoll syndrome, Malakoplakia, Mallory-Weiss syndrome, Meckel syndrome, Megacystis microcolon intestinal hypoperistalsis syndrome, Megaduodenum and/or megacystis, Menetrier disease, Mental retardation skeletal dysplasia abducens palsy, Microgastria limb reduction defect, Microphthalmia syndromic 9, Microphthalmia with linear skin defects syndrome, Microvillus inclusion disease, Mitochondrial neurogastrointestinal encephalopathy syndrome, MOGS-CDG (CDG-IIb), MPI-CDG (CDG-Ib), MPV17-related hepatocerebral mitochondrial DNA depletion syndrome, Muir-Torre syndrome, Multiple endocrine neoplasia type 1, Multiple endocrine neoplasia type 2A, Multiple endocrine neoplasia type 2B, Multisystemic smooth muscle dysfunction syndrome, MURCS association, Necrotizing enterocolitis, Neonatal adrenoleukodystrophy, Neonatal hemochromatosis, Nodular regenerative hyperplasia, Occipital horn syndrome, Omphalocele cleft palate syndrome lethal, Omphalocele, exstrophy of the cloaca, imperforate anus, and spinal defects complex, Omphalomesenteric cyst, Pallister-Hall syndrome, Pallister-Killian mosaic syndrome, Pancreatic adenoma, Pancreatic cancer, Pearson syndrome, Pediatric Crohn's disease, Pediatric ulcerative colitis, Pentalogy of Cantrell, Peutz-Jeghers syndrome, PGM1-CDG, Plummer Vinson syndrome, PMM2-CDG (CDG-Ia), Polycystic liver disease, Primary biliary cholangitis, Primary intestinal lymphangiectasia, Primary liver cancer, Primary sclerosing cholangitis, Progressive familial intrahepatic cholestasis 1, Progressive familial intrahepatic cholestasis type 2, Progressive familial intrahepatic cholestasis type 3, Progressive familial intrahepatic cholestasis-4, Pseudomyxoma peritonei, Refsum disease, infantile form, Renal nutcracker syndrome, Retroperitoneal fibrosis, Reynolds syndrome, RFT1-CDG (CDG-In), Ring chromosome 13, Rotor syndrome, Sandifer syndrome, Satoyoshi syndrome, SCARF syndrome, Sclerosing mesenteritis, Short rib-polydactyly syndrome type 3, Shprintzen omphalocele syndrome, Shwachman-Diamond syndrome, Simpson-Golabi-Behmel syndrome, Sirenomelia, Small Intestinal Adenocarcinoma, Splenogonadal fusion limb defects micrognatia, Stalker Chitayat syndrome, STAR syndrome, Superior mesenteric artery syndrome, Syndromic microphthalmia, type 3, Thoraco abdominal enteric duplication, TMEM165-CDG (CDG-IIk), Townes-Brocks syndrome, Transient infantile liver failure, Trichohepatoenteric syndrome, Triple A syndrome, Trisomy 13, Trisomy 18, Tufting enteropathy, Tylosis with esophageal cancer, Tyrosinemia type 1, Ulnar-mammary syndrome, VACTERL association, VIPoma, Waardenburg syndrome type 4, Watermelon stomach, Whipple disease, Wilson disease, Wolf-Hirschhorn syndrome, Wolman disease, Wrinkly skin syndrome, Zellweger syndrome, Zollinger-Ellison syndrome, Hemorrhoids, Pancreatitis, Peptic ulcer disease, Small Intestinal Bacterial Overgrowth, Constipation, and Leaky gut, among others. Digestive biomarker 108 may include receiving a digestive signal form a sensor. "Digestive signal" is a datum that relates to and/or represents an element associated with the status of an individual's digestive system. As a non-limiting example, a digestive signal may include an image of an esophagus, stomach, intestines, rectum, or mouth. As a further non-limiting example, a digestive signal may include one or more lights, voltages, currents, sounds, chemicals, pressures, and the like from a sensor. A "sensor", for the purposes of this disclosure, is a device that records, monitors, stores, measures, and/or transmits digestive signals. As a non-limiting example, a sensor may include an imaging sensors, such as optical cameras, infrared cameras, 3D cameras, multispectral cameras, hyperspectral cameras, polarized cameras, chemical sensors, motion sensors, ranging sensors, light radar components, detection or imaging using radio frequency component like radar, terahertz or millimeter waves imagers, seismic sensors, magnetic sensors, weight/mass sensors, ionizing radiation sensors, and/or acoustical sensors. As a further non-limiting example, a sensor may include one or more medical devices that at least detect and/or monitor an individual's digestive system, such as semi-auto analyzers, photo colorimeters, cell photo colorimeters, hemoglobin meters, mass spectrometers, chromatographic instruments, and the like. Digestive biomarker 108 may include biomarkers relating to a user that would indicate a digestive disease such as FAS, tumor necrosis factor a, FADD, TNF receptor-associated death domain (TRADD), receptor-interacting protein (RIP) kinase 1, mtDNA, AST, cyctochrone c, glutamate dehydrogenase (GLDH), carbamoyl phosphate synthetase 1, nitrotyrosine, protein caronyls, oxidized albumin, oxidized DNA, lipid peroxidation products, interleukins, cytokines, N-formyl peptides, bile acids, gut microflora (e.g., firmicutes, Bacteroidetes, actinobacteria, proteobacteria), parasitic infestations, (e.g., tape worms, hook worms, ascarids, schistosomiasis, giardia, *Enterobius vermicularis, Ancylostoma duodenale, Necator americanus, entamoeba histolytica,* etc.) and the like. Digestive biomarker 108 may include biomarkers relating to symptoms of a digestive disease such as extreme fatigue, bleeding (from orifices), bloating, constipation, diarrhea, heartburn, incontinence, loss of appetite, pain in the belly, nausea, vomiting, weight loss, weight gain, swallowing problems, and changes in sleep pattern.

Computing device 104 generates at least a digestive parameter 112 of a plurality of digestive parameter 112 as a function of the digestive biomarker 108. A "digestive parameter," for the purposes of this disclosure, is a measurable value associated with a user's digestive system. As a non-limiting example, digestive parameters may include glucose level, carbohydrate level, lipid levels, protein levels, fatty acid levels, glycerol levels, amino acid levels, gluten sensitivity, dairy sensitivity, digestion, nutrient absorption, body fat percentage, one or more chemical concentrations, pancreatic juice levels, bile levels, enzyme levels and hormone levels, among others. Nutrient absorption is a measure of how well the human gut receives nutrients from food, supplements, vitamins, and the like. A majority of nutrients are absorbed in the jejunum, with the following exceptions: iron is absorbed in the duodenum, vitamin B12 by passive diffusion through the small intestine, folate (vitamin B9) is absorbed in the duodenum and jejunum, vitamin B12 is absorbed in the terminal ileum, water is absorbed by osmosis and lipid by passive diffusion through small intestine, sodium bicarbonate is absorbed by active transport and glucose and amino acid co-transport, and fructose is absorbed by facilitated diffusion. Digested food is now able to pass into the blood vessels in the wall of the intestine through either diffusion or active transport. The small intestine 432 is the site where most of the nutrients from ingested food are absorbed. The inner wall, or mucosa, of the small intestine 432, is lined with simple columnar epithelial tissue. Structurally, the mucosa is covered in wrinkles or folds called plicae circulares, which are considered permanent features in the wall of the organ. They are distinct from rugae which are considered non-permanent or temporary allowing for distention and contraction. From the plicae circulares project microscopic finger-like pieces of tissue called villi. The individual epithelial cells also have finger-like projections known as microvilli. The functions of the plicae circulares, the villi, and the microvilli are to increase the amount of surface area available for the absorption of nutrients, and to limit the loss of said nutrients to intestinal fauna. Each villus has a network of capillaries and fine lymphatic vessels called lacteals close to its surface. The epithelial cells of the villi transport nutrients from the lumen of the intestine into these capillaries (amino acids and carbohydrates) and lacteals (lipids). The absorbed substances are transported via the blood vessels to different organs of the body where they are used to build complex substances such as the proteins required by our body. The material that remains undigested and unabsorbed passes into the large intestine 436. The small intestine 432 supports the body's immune system. The presence of gut flora appears to contribute positively to the host's immune system. Therefore, absorption condition 124 may include a measure of or contribute to the user's immune health. Peyer's patches, located within the ileum of the small intestine 432, are an important part of the digestive tract's local immune system. They are part of the lymphatic system, and provide a site for antigens from potentially harmful bacteria or other microorganisms in the digestive tract to be sampled, and subsequently presented to the immune system. Digestive parameter 112 may be generated as a function of a digestive algorithm. The digestive algorithms include algorithms used in gastroenterology, gastrointestinal endoscopy, Computer-Aided Diagnosis (CADx) for EGC diagnosis, CADx for cancer staging and estimation of invasion depth, AI system for automated lesion delineation, and AI systems for *H. pylori* infection prediction.

Still referring to FIG. 1, computing device 104 determines digestive profile 116 as a function of the at least a digestive 112 wherein the digestive profile 116. A "digestive profile," for the purposes of this disclosure, is a profile of a user's digestive state of health according to a plurality of digestive parameters. Digestive profile 116, as a non-limiting example, may include enzyme level, digestive processes, and pancreas juice composition. Digestive profile 116 may include parameters chosen specifically due to a digestive deficiency. A "digestive deficiency", for the purposes of this disclosure, is an inadequacy and/or deficiency of a digestive parameter compared to a digestive threshold. A "digestive threshold," for the purposes of this disclosure, is a range of a digestive parameter, limit, maximum, or minimum thereof that constitutes healthy or normal digestive parameter 112. Digestive threshold may be defined, in a non-limiting example, by American Medical Association, and the American College of Physicians, among others. Digestive threshold may be defined, in a further non-limiting example, in guidelines included in one or more medical journals, such as the Lancet, New England Journal of Medicine, Science, Journal of American Medical Association, and the like thereof.

Still referring to FIG. 1, digestive profile 116 includes a quantitative digestive health score 120. A "digestive health score" for the purposes of this disclosure, is a quantitative value assigned to digestive profile as a function of the digestive parameters and their relationship to the digestive threshold associated with the digestive parameter. In a non-limiting example, enzyme level may be a digestive parameter, and be assigned a first weight. Enzyme level may be above the maximum defined in enzyme level digestive threshold and would then be given a quantitative score. This would be done to a plurality of digestive parameters 112 within digestive profile 116 and then summed to produce digestive health score 120. The weights associated with each digestive parameter may be personalized to the user, or the same for every user.

Still referring to FIG. 1, digestive profile 116 includes absorption condition 124 correlated to at least a digestive parameter 112. "Absorption condition", for the purposes of this disclosure, is the ability for the digestive system of a user to absorb nutrients from nutrition elements consistent with this disclosure. Absorption condition 124 may be the ability of any portion of the digestive system to absorb nutrients related to at least a digestive parameter. Absorption condition 124 may include a location of the absorption condition may be consistent with the above parameters, biomarkers, or the like. Absorption condition 124 wherein the absorption condition is correlated to increased intestinal permeability. Absorption condition 124 wherein the absorption condition is correlated to decreased intestinal permeability. "Intestinal permeability", for the purposes of this disclosure, is how easily substances pass through the intestinal wall. Intestinal permeability is directly correlated to absorption of nutrients through any part of the intestines, colloquially known as a the "gut".

Still referring to FIG. 1, computing device 104 identifies at least a nutrition element 128 as function of the digestive profile 116. "Nutrition element", as used in this disclosure, is a source of nourishment that may be consumed by a user such that the user may absorb nutrients from the nutrition element. In a non-limiting example, nutrition element 128 may include plants, meats, animal products, fungi, seeds, nuts, legumes, fruits, dairy, milk, eggs, cereals, grains, seafood, dried foods, dumplings, pies, noodles, salads, stews, soups, sauces, sandwiches, and the like. Computing device 104 may identify the plurality of nutrition elements 128 by classifying the digestive profile 116 to a digestive disease category. A "digestive disease category", for the purposes of this disclosure, is the grouping of diseases by some common element within the disease category. The digestive disease profile 116 includes a quantitative digestive health score 120 related to the at least a digestive parameter 112 and absorption condition 124 related to the at least a digestive parameter 112. In a non-limiting example, a category of digestive disease may be genetic diseases, onset diseases, or environmental diseases. Computing device 104 may then identify the plurality of nutrition elements 128 according to the digestive disease category, wherein the plurality of nutrition elements may be specifically tailored to that category. Computing device 104 obtains at least a nutrient composition 132 correlated to at least a nutrition element 128. Nutrient composition 132 may include a list and/or compilation of all of the nutrients contained in a nutrition element 128. Nutrient composition 132 may include one or more quantities and/or amounts of total fat, including saturated fat and/or trans-fat, cholesterol, sodium, total carbohydrates, including dietary fiber and/or total sugars, protein, vitamin A, vitamin C, thiamin, riboflavin, niacin, pantothenic acid, vitamin b6, folate, biotin, vitamin B12, vitamin D, vitamin E, vitamin K, calcium, iron, phosphorous, iodine, magnesium, zinc, selenium, copper, manganese, chromium, molybdenum, chloride, and the like thereof. Nourishment composition 132 may be obtained from a directory, database, library, or other data store where nutrient composition 132 may be stored. Computing device 104 may determine a nourishment score 136 as a function of the effect of the nutrition element 128 on the digestive profile 116. A "nourishment score", for the purposes of this disclosure, is a quantitative value associated with the effectiveness of the nutrition element, which is comprised of nutrients, on the digestive profile.

With continued reference to FIG. 1, determining nourishment scores 136 by generating training data using the plurality of nutrition elements 128 identified according to the digestive disease category. Training data may be generated in a plurality of methods including, but not limited to: databases, datastores, expert inputs, hospital records, medical records, test results, prior diagnoses data, and user inputs, among others. Training data may correlate machine-learning model inputs to machine-learning model outputs consistent with the entirety of this disclosure. Computing device 104 trains a nutrition element machine-learning model 140 according to the training data entries that correlate the nourishment score 136 for each digestive disease category to nutrient composition 132.

Still referring to FIG. 1, nutrition element machine-learning model may include a machine-learning model configured to produce a nutrition element output given nourishment compositions and nourishment deficiencies as inputs; this is in contrast to a non-machine learning software program where the commands to be executed are determined in advance by a user and written in a programming language. Nutrition element machine-learning model 140 may include one or more nutrition element machine-learning processes such as supervised, unsupervised, or reinforcement machine-learning processes that computing device 104 and/or a remote device may or may not use in the determination of nutrition element 128. As used in this disclosure "remote device" is an external device to computing device 104. An nutrient element machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train nutrition element machine-learning process as a function of a nutrition element training set. As used in this disclosure a "nutrition element training set" is a training set that correlates at least nutrient composition and digestive profile to nourishment score. For example, and without limitation, nourishment composition of 14 g of protein and 2 g of fiber and a digestive profile indicating low levels of protein due to Crohn's disease may relate to a nutrition element of salmon. The nutrition element training set may be received as a function of user-entered valuations of nourishment compositions, nourishment deficiencies, and/or nutrition elements. Computing device 104 may receive nutrition element training set by receiving correlations of nourishment compositions and/or nourishment deficiencies that were previously received and/or determined during a previous iteration of determining nutrition elements. The nutrition element training set may be received by one or more remote devices that at least correlate a nourishment composition and nourishment deficiency to a nutrition element 128, wherein a remote device is an external device to computing device 104, as described above.

Still referring to FIG. 1, nutrition element machine-learning model 140 may identify nutrition element 128 as a function of one or more classifiers. A "classifier," as used in this disclosure is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Computing device 104 and/or another device may generate a classifier using a classification algorithm, defined as a processes whereby a computing device 104 derives a classifier from training data. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 1, computing device 104 may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as P(A/B)=P(B/A) P(A)÷1P(B), where P(AB) is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming training data into a frequency table. Computing device 104 may then calculate a likelihood table by calculating probabilities of different data entries and classification labels. Computing device 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 1, computing device 104 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute/as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

Still referring to FIG. 1, computing device 104 may receive nutrition element machine-learning model 140 from the remote device that utilizes one or more nutrition element machine learning processes, wherein a remote device is described above in detail. For example, and without limitation, a remote device may include a computing device, external device, processor, and the like thereof. The remote device may perform the nutrition element machine-learning process using the nutrition element training set to generate nutrition element 128 and transmit the output to computing device 104. The remote device may transmit a signal, bit, datum, or parameter to computing device 104 that at least relates to nutrition element 128. Additionally or alternatively, the remote device may provide an updated machine-learning model. For example, and without limitation, an updated machine-learning model may be comprised of a firmware update, a software update, an nutrition element machine-learning process correction, and the like thereof. As a non-limiting example a software update may incorporate a new nourishment composition that relates to a modified nourishment deficiency. Additionally or alternatively, the updated machine learning model may be transmitted to the remote device, wherein the remote device may replace the nutrition element machine-learning model with the updated machine-learning model and determine the nutrition element 128 as a function of the nourishment deficiency using the updated machine-learning model. The updated machine-learning model may be transmitted by the remote device and received by computing device 104 as a software update, firmware update, or corrected nutrition element machine-learning model. For example, and without limitation a nutrition element machine-learning model may utilize a neural net machine-learning process, wherein the updated machine-learning model may incorporate polynomial regression machine-learning process. Updated machine learning model may additionally or alternatively include any machine-learning model used as an updated machine learning model as described in U.S. Nonprovisional application Ser. No. 17/106,658, filed on Nov. 30, 2020, and entitled "A SYSTEM AND METHOD FOR GENERATING A DYNAMIC WEIGHTED COMBINATION," the entirety of which is incorporated herein by reference.

Computing device 104 determines nourishment score as a function of the nutrition element machine-learning model 140 and the digestive profile 116. Nourishment score 136 may indicate that a nutrition element 128 has a positive effect on digestive profile 116. Nourishment score 136 may be higher for nutrition elements 128 that raise digestive health score 120. Identifying nutrition element 128 as a function of the nourishment score 136 and nutrition element machine-learning model 140. Identifying nutrition elements 128 may include identifying the nutrition elements that have a positive impact on the absorption condition. A positive impact may, for example, include increasing nutrient absorption in the large or small intestine back to a normal level from which is has deteriorated. In another non-limiting example, a positive impact on absorption may include decreasing elevated levels of nutrient absorption in the large or small intestine back to a normal level from which it has spiked out of control. Identifying nutrition elements 128 may include identifying the nutrition elements that have a negative impact on the absorption condition. A negative impact on absorption may include, in a non-limiting example, nutrition elements that lower absorption level from a normal level to a lower-than-normal level. In another non-limiting example, a negative impact on absorption may include nutrition elements that increase nutrient absorption levels in the small or large intestine from a normal level to a higher-than-normal level of absorption. Identifying the plurality of nutrition elements 128 may include identifying nutrition elements 128 intended to prevent digestive disease according to the digestive disease category. Preventing digestive disease according to the digestive disease category by identifying nutrition elements may include suggesting nutrition elements that improve digestive disease by improving the common element in the digestive disease category. For example, nutrition elements that lower cholesterol may be suggested for a digestive disease category wherein decreased absorption is the common element. In a non-limiting embodiment, leafy green vegetables may be suggested as nutrition elements to increase absorption in a user that has leaky gut, wherein decreased absorption is a digestive parameter.

Still referring to FIG. 1, computing device 104 generates nourishment program 144 as a function of the nourishment score 136 and the digestive profile 116, wherein the digestive profile 116 includes the digestive health score 120 and the absorption condition 124. Generating the digestive disease nourishment program 144 may include generating an adherence score, wherein the adherence score reflects the level of user participation in the digestive nourishment program. "Digestive disease nourishment program", for the purposes of this disclosure, is a suggested nourishment program that may include foods, meals, supplements, vitamins, and minerals, among others, intended to improve the digestive disease state of the user. Adherence may be measured by user input to a meal tracker application, notebook, list, computer application, or the like. Adherence score may grant points to a user for following a suggested meal plan, such as digestive disease nourishment plan 144. Adherence score, in a non-limiting example, may include weighted values which value some nutrition elements 128 more than others, and that weight may be correlated to nourishment score 136. Adherence score may seek to maximize nourishment score 136 in any subset of nourishment program 144. Adherence score may include calculating a change in numerical digestive health score 120, wherein a positive change in health score 120 over a period of time would indicate a high adherence score and a negative change in health score 120 would indicate a low adherence score. In non-limiting embodiments, adherence score may be generated at the generation of nourishment program 144 and consistently and periodically updated throughout the nourishment program 144.

Still referring to FIG. 1, computing device 104 may generate digestive disease nourishment program 144, wherein generating digestive disease nourishment program 144 may include receiving at least a user preference regarding the at least a nutrition element 128. The user preference may include user selection of nutrition elements 128 like foods the user prefers, food the user wishes to not consume, food alternates, wherein a user may select a food nutritionally similar to a suggested nutrition element, allergy requirements, food intolerance preferences, and the like. User preferences may increase adherence score by including foods a user is more likely to eat and excluding foods a user cannot or will not consume. Computing device 104 may modify nutrition element 128 as a function of the user preference. Computing device 104 may modify digestive nourishment program 144 by switching, adding, deleting, or otherwise altering nutrition elements 128 within the program.

Still referring to FIG. 1, computing device 104 may generate digestive disease nourishment program 144 by generating a nourishment classifier. Computing device 104 may generate digestive disease nourishment program 144 by training the nourishment classifier as a function of a classification machine-learning and a training set relating nutrient composition 132 and nourishment score 136 to nutrition elements 128. Computing device 104 may then output the nourishment program classifier as a function of the nourishment program classifier, nutrition elements 128, nutrient composition 132, and nourishment score 136. Computing device 104 may then compile the plurality of nutrition elements 128 to achieve the nourishment score 136, wherein the nourishment score 136 may be sought to be maximized to benefit the user. High nourishment score 136 may increase adherence score and therefore also digestive health score 120.

Still referring to FIG. 1, computing device 104 may train classification machine-learning process as a function of a nourishment training set. As used in this disclosure a "nourishment training set" is a training set that correlates nutrition elements to nutrient compositions. The nourishment training set may be received as a function of user-entered nutrition elements 128, intendent outcomes, and/or nourishment programs. Computing device 104 may receive nourishment training by receiving correlations of nutrition elements and nutrient compositions that were previously received and/or determined during a previous iteration of determining nourishment programs. The nourishment training set may be generated by any of the methods disclosed hereinabove, or another method undisclosed. The nourishment training set may be received by one or more remote devices that correlate a nutrition element and/or nutrient compositions to a nourishment program, wherein a remote device is an external device to computing device 104, as described above.

Still referring to FIG. 1, computing device 104 may receive classification machine-learning model from the remote device that utilizes one or more classification machine learning processes, wherein a remote device is described above in detail. For example, and without limitation, a remote device may include a computing device, external device, processor, and the like thereof. The remote device may perform the classification machine-learning process using the nourishment training set to generate nourishment program 144 and transmit the output to computing device 104. The remote device may transmit a signal, bit, datum, or parameter to computing device 104 that at least relates to nourishment program 144. Additionally or alternatively, the remote device may provide an updated machine-learning model. For example, and without limitation, an updated machine-learning model may be comprised of a firmware update, a software update, a classification machine-learning process correction, and the like thereof. As a non-limiting example, a software update may incorporate a new intended outcome that relates to a modified edible. Additionally or alternatively, the updated machine learning model may be transmitted to the remote device, wherein the remote device may replace the classification machine-learning model with the updated machine-learning model and determine the nourishment program as a function of the intended outcome using the updated machine-learning model. The updated machine-learning model may be transmitted by the remote device and received by computing device 104 as a software update, firmware update, or corrected classification machine-learning model. For example, and without limitation classification machine-learning model may utilize a nearest neighbor machine-learning process, wherein the updated machine-learning model may incorporate association rules machine-learning processes.

Figure 2:
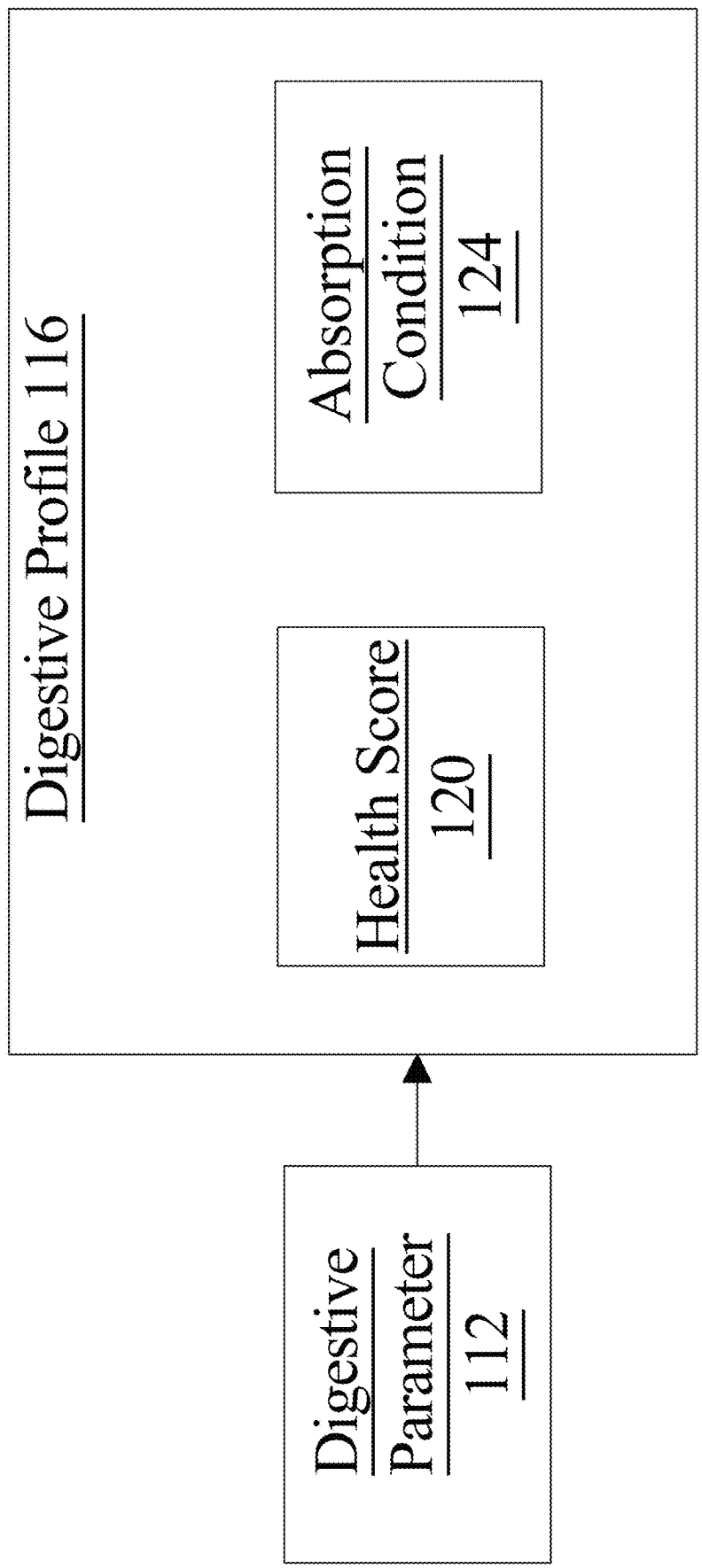
FIG. 2 is a representative diagram of an exemplary embodiment of digestive parameters according to an embodiment of the invention.

Now referring to FIG. 2, digestive profile 116 may include digestive health score 120. Digestive profile 116 may include absorption condition 124. Digestive health score 120 may be a numerical value that acts as a summary of a user's digestive health as a function of the plurality of digestive parameters 112 and their respective digestive thresholds. Any number or combination of mathematical manipulations may be performed on any number or combination of digestive parameters 112 to generate digestive health score 120. Absorption condition 124 may include a location, severity, type, level, nutrient and other absorption information. Absorption condition 124 may include the duration of the absorption deficiency or excess and may suggest what treatment would be suitable for the user based on absorption condition 124. Digestive profile 116, which is determined as a function of digestive parameters 112, may be updated over time to reflect improvement or decline in user's digestive disease state condition.

Figure 3:
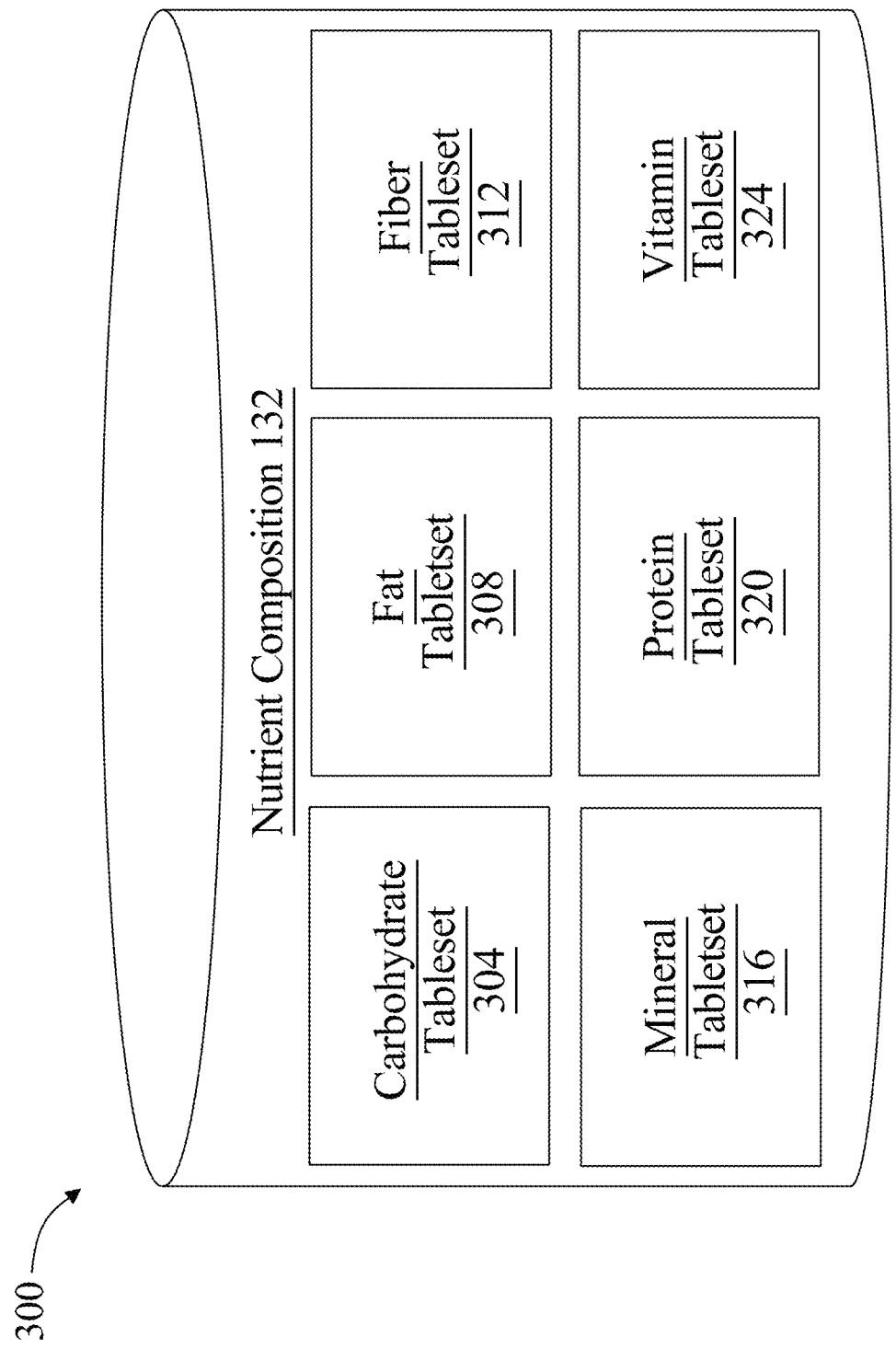
FIG. 3 is a representative diagram of an exemplary datastore of nutrient composition according to an embodiment of the invention.

Now referring to FIG. 3, an exemplary datastore 300 storing plurality of nutrient compositions 132 according to an embodiment of the invention is illustrated. Nutrient composition 132 may be implemented, without limitation, as a relational databank, a key-value retrieval databank such as a NOSQL databank, or any other format or structure for use as a databank that a person skilled in the art would recognize as suitable upon review of the entirety of this disclosure. Nutrient composition 132 may alternatively or additionally be implemented using a distributed data storage protocol and/or data structure, such as a distributed hash table or the like. Nutrient composition 132 may include a plurality of data entries and/or records as described above. Data entries in a databank may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a databank may store, retrieve, organize, and/or reflect data and/or records as used herein, as well as categories and/or populations of data consistently with this disclosure. Nutrient composition 132 may include a carbohydrate tableset 304. Carbohydrate tableset 304 may relate to a nourishment composition of an nutrition element with respect to the quantity and/or type of carbohydrates in the nutrition element. As a non-limiting example, carbohydrate tableset 304 may include monosaccharides, disaccharides, oligosaccharides, polysaccharides, and the like thereof. Nutrient composition 132 may include a fat tableset 308. Fat tableset 308 may relate to a nourishment composition of an nutrition element with respect to the quantity and/or type of esterified fatty acids in the nutrition element. Fat tableset 308 may include, without limitation, triglycerides, monoglycerides, diglycerides, phospholipids, sterols, waxes, and free fatty acids. Nutrient composition 132 may include a fiber tableset 312. Fiber tableset 312 may relate to a nourishment composition of a nutrition element with respect to the quantity and/or type of fiber in the nutrition element. As a non-limiting example, fiber tableset 312 may include soluble fiber, such as beta-glucans, raw guar gum, *psyllium*, inulin, and the like thereof as well as insoluble fiber, such as wheat bran, cellulose, lignin, and the like thereof. Nutrient composition 132 may include a mineral tableset 316. Mineral tableset 316 may relate to a nourishment composition of a nutrition element with respect to the quantity and/or type of minerals in the nutrition element. As a non-limiting example, mineral tableset 316 may include calcium, phosphorous, magnesium, sodium, potassium, chloride, sulfur, iron, manganese, copper, iodine, zing, cobalt, fluoride, selenium, and the like thereof. Nutrient composition 132 may include a protein tableset 320. Protein tableset 320 may relate to a nourishment composition of a nutrition element with respect to the quantity and/or type of proteins in the nutrition element. As a non-limiting example, protein tableset 320 may include amino acids combinations, wherein amino acids may include, without limitation, alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, and the like thereof. Nutrient composition 132 may include a vitamin tableset 324. Vitamin tableset 324 may relate to a nourishment composition of a nutrition element with respect to the quantity and/or type of vitamins in the nutrition element. As a non-limiting example, vitamin tableset 324 may include vitamin A, vitamin $B_1$, vitamin B2, vitamin B3, vitamin $B_5$, vitamin B6, vitamin B7, vitamin B9, vitamin B12, vitamin C, vitamin D, vitamin E, vitamin K, and the like thereof.

Figure 4:
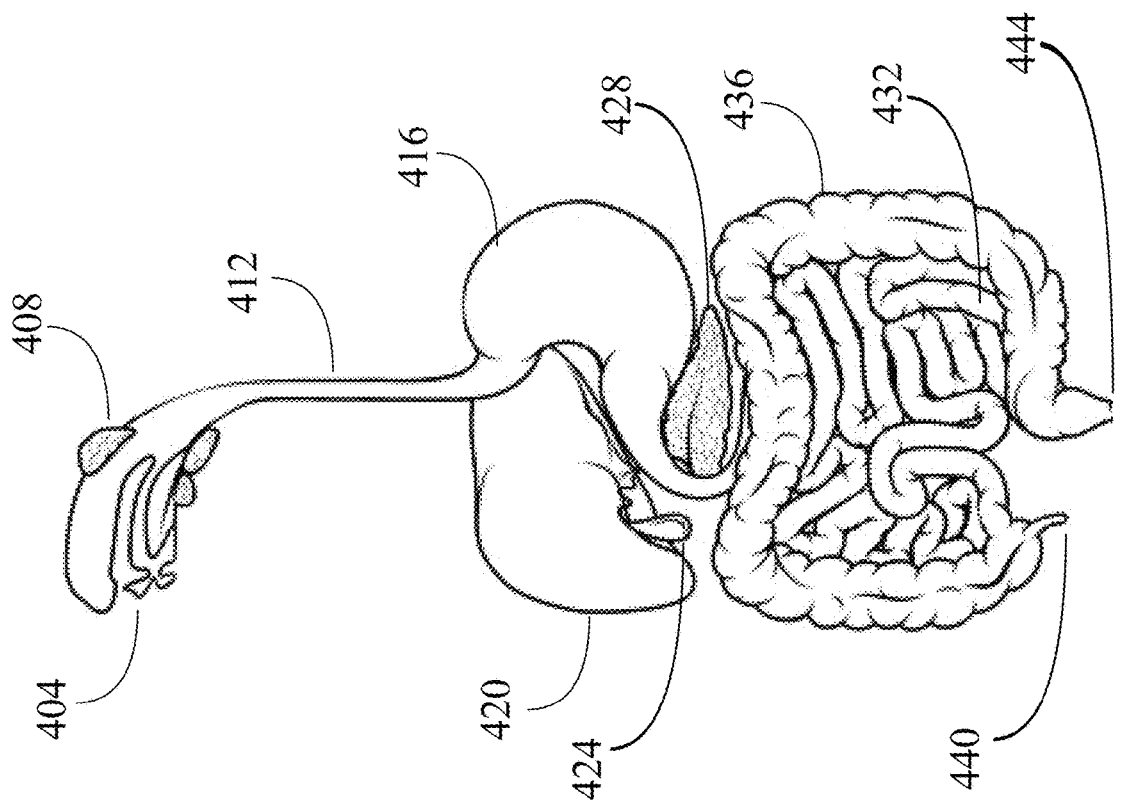
FIG. 4 is a representative diagram of an exemplary embodiment of the human digestive system and biomarkers thereof that can be received as a digestive biomarker according to an embodiment of the invention.

Referring now to FIG. 4, an illustrative embodiment of digestive system 400 is illustrated in diagrammatic view. Digestive system 400 may include digestive biomarkers 108 and may generate or measure digestive parameters 112 as a function thereof. Digestive system 400 includes the mouth 404 and salivary glands 408. Digestive biomarkers 108 may include sample received from any of the components of digestive system 400. For example, and without limitation, mouth 404 and salivary glands 408 may include saliva samples. Digestive system 400 may include esophagus 412.

Esophagus 412 may include hematomas, bleeding, biopsies, and the like. Digestive system 400 includes stomach 416. Stomach 416 may include bacteria, stomach pain, inability to drink fluids, extreme hunger even after eating, and the like. Digestive system 400 includes liver 420. Digestive system 400 includes gallbladder 424. Digestive system 400 includes pancreas 428. Digestive system 400 includes small intestine 432. Small intestine 432 includes jejunum, duodenum, and ileum. The interior of the small intestine 432 is exposed to digestive food, it includes finger-like projections of mucosa, called villi. The small intestine 432 is the main component responsible for absorption and therefore absorption condition 124. The small intestine 432 is where most chemical digestion takes place. Many of the digestive enzymes that act in the small intestine 432 are secreted by the pancreas 428 and liver 420 and enter the small intestine 432 via the pancreatic duct. Pancreatic enzymes and bile from the gallbladder 424 enter the small intestine 432 in response to the hormone cholecystokinin, which is produced in the small intestine 432 in response to the presence of nutrients. Secretin, another hormone produced in the small intestine, causes additional effects on the pancreas 428, where it promotes the release of bicarbonate into the duodenum in order to neutralize the potentially harmful acid coming from the stomach 416. The three major classes of nutrients that undergo digestion are proteins, lipids (fats) and carbohydrates. Proteins are degraded into small peptides and amino acids before absorption.[19] Chemical breakdown begins in the stomach and continues in the small intestine 432. Proteolytic enzymes, including trypsin and chymotrypsin, are secreted by the pancreas and cleave proteins into smaller peptides. Carboxypeptidase, which is a pancreatic brush border enzyme, splits one amino acid at a time. Aminopeptidase and dipeptidase free the end amino acid products. Lipids (fats) are degraded into fatty acids and glycerol. Pancreatic lipase breaks down triglycerides into free fatty acids and monoglycerides. Pancreatic lipase works with the help of the salts from the bile secreted by the liver 420 and stored in the gallbladder. Bile salts attach to triglycerides to help emulsify them, which aids access by pancreatic lipase. This occurs because the lipase is water-soluble but the fatty triglycerides are hydrophobic and tend to orient towards each other and away from the watery intestinal surroundings. The bile salts emulsify the triglycerides in the watery surroundings until the lipase can break them into the smaller components that are able to enter the villi for absorption. Some carbohydrates are degraded into simple sugars, or monosaccharides (e.g., glucose). Pancreatic amylase breaks down some carbohydrates (notably starch) into oligosaccharides. Other carbohydrates pass undigested into the large intestine 436 and further handling by intestinal bacteria. Brush border enzymes take over from there. The most important brush border enzymes are dextrinase and glucoamylase, which further break down oligosaccharides. Other brush border enzymes are maltase, sucrase and lactase. Lactase is absent in some adult humans and, for them, lactose (a disaccharide), as well as most polysaccharides, is not digested in the small intestine. Some carbohydrates, such as cellulose, are not digested at all, despite being made of multiple glucose units. This is because the cellulose is made out of beta-glucose, making the inter-monosaccharidal bindings different from the ones present in starch, which consists of alpha-glucose. Humans lack the enzyme for splitting the beta-glucose-bonds, something reserved for herbivores and bacteria from the large intestine 436. Digestive system 400 includes large intestine 436, wherein salt levels, water levels, and material analysis may be used as digestive parameter 112. Digestive system 400 includes appendix 440. Digestive system 400 includes rectum 444, wherein stool texture, stool amount, stool consistency, and electrical signals to and from the brain may be digestive parameter 112 or even submitted as digestive biomarker 108.

Figure 5:
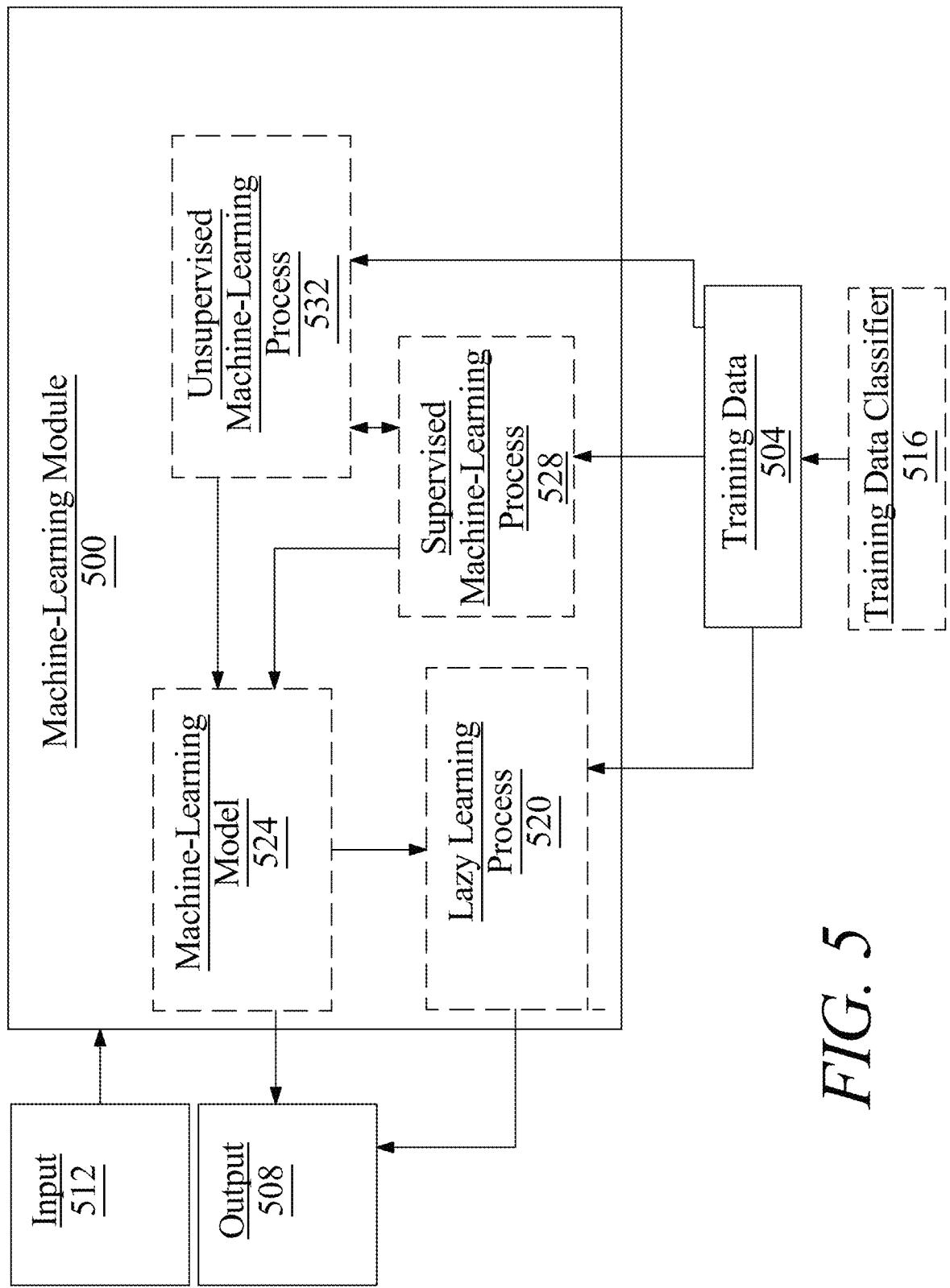
FIG. 5 is a block diagram of an exemplary embodiment of a machine-learning module.

Referring now to FIG. 5, an exemplary embodiment of a machine-learning module 500 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 504 to generate an algorithm that will be performed by a computing device/module to produce outputs 508 given data provided as inputs 512; this is in contrast to a non-machine learning software program where the commands to be executed are determined in advance by a user and written in a programming language.

Still referring to FIG. 5, "training data," as used herein, is data containing correlations that a machine-learning process may use to model relationships between two or more categories of data elements. For instance, and without limitation, training data 504 may include a plurality of data entries, each entry representing a set of data elements that were recorded, received, and/or generated together; data elements may be correlated by shared existence in a given data entry, by proximity in a given data entry, or the like. Multiple data entries in training data 504 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 504 according to various correlations; correlations may indicate causative and/or predictive links between categories of data elements, which may be modeled as relationships such as mathematical relationships by machine-learning processes as described in further detail below. Training data 504 may be formatted and/or organized by categories of data elements, for instance by associating data elements with one or more descriptors corresponding to categories of data elements. As a non-limiting example, training data 504 may include data entered in standardized forms by persons or processes, such that entry of a given data element in a given field in a form may be mapped to one or more descriptors of categories. Elements in training data 504 may be linked to descriptors of categories by tags, tokens, or other data elements; for instance, and without limitation, training data 504 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 5, training data 504 may include one or more elements that are not categorized; that is, training data 504 may not be formatted or contain descriptors for some elements of data. Machine-learning algorithms and/or other processes may sort training data 504 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 504 to be made applicable for two or more distinct machine-learning algorithms as described in further detail below. Training data 504 used by machine-learning module 500 may correlate any input data as described in this disclosure to any output data as described in this disclosure. As a non-limiting illustrative example nourishment scores and nutrient compositions may be inputs, wherein a nutrition element is outputted.

Further referring to FIG. 5, training data may be filtered, sorted, and/or selected using one or more supervised and/or unsupervised machine-learning processes and/or models as described in further detail below; such models may include without limitation a training data classifier 516. Training data classifier 516 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 500 may generate a classifier using a classification algorithm, defined as a processes whereby a computing device and/or any module and/or component operating thereon derives a classifier from training data 504. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 516 may classify elements of training data to classes of deficiencies, wherein a nourishment deficiency may be categorized to a large deficiency, a medium deficiency, and/or a small deficiency.

Still referring to FIG. 5, machine-learning module 500 may be configured to perform a lazy-learning process 520 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 504. Heuristic may include selecting some number of highest-ranking associations and/or training data 504 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 5, machine-learning processes as described in this disclosure may be used to generate machine-learning models 524. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 524 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 524 may be generated by creating an artificial neural network, such as a convolutional neural network comprising an input layer of nodes, one or more intermediate layers, and an output layer of nodes. Connections between nodes may be created via the process of "training" the network, in which elements from a training data 504 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 5, machine-learning algorithms may include at least a supervised machine-learning process 528. At least a supervised machine-learning process 528, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include nutrient compositions and/or nourishment scores as described above as inputs, nutrition elements as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 504. Persons skilled in the art, upon reviewing the entirety of this disclosure, will be aware of various possible variations of at least a supervised machine-learning process 528 that may be used to determine relation between inputs and outputs. Supervised machine-learning processes may include classification algorithms as defined above.

Further referring to FIG. 5, machine learning processes may include at least an unsupervised machine-learning processes 532. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 5, machine-learning module 500 may be designed and configured to create a machine-learning model 524 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 5, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Figure 6:
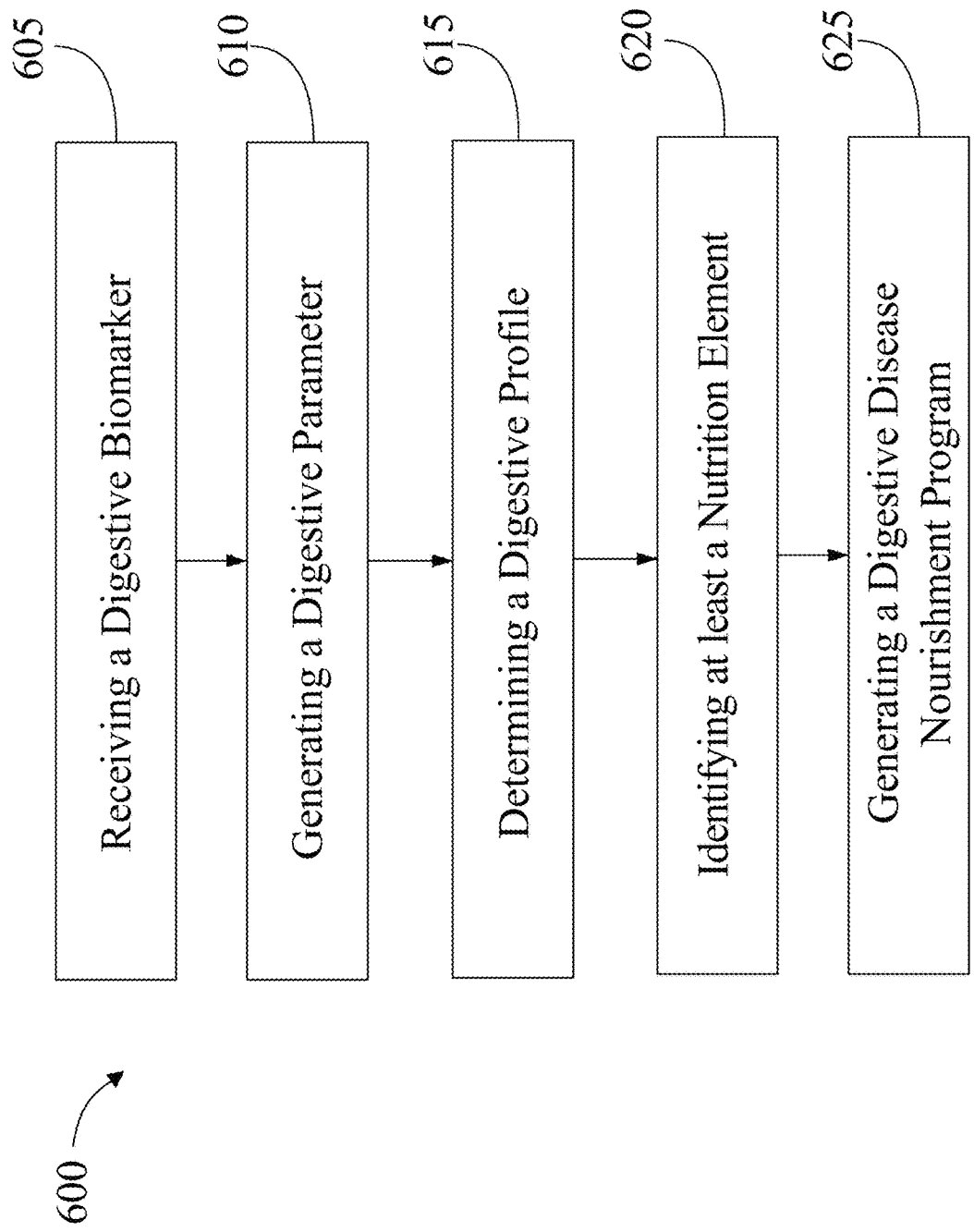
FIG. 6 is a process flow diagram illustrating an exemplary embodiment of a method of generating a digestive disease nourishment plan.

Referring now to FIG. 6, an exemplary method 600 for generating a digestive disease nourishment program is presented. At step 605, a computing device 604 receives at least a digestive biomarker 108 relating to a user. Computing device 104 includes any of the computing devices 104 as described herein. Digestive biomarker 108 includes any of the digestive biomarkers 108 as described herein. Receiving the at least a digestive biomarker 108 may include receiving a result of one or more tests relating to the user. Receiving the at least a digestive biomarker 108 may include receiving a prior diagnosis of a digestive disease relating to the user, including a prior diagnosis of celiac disease. relating to the user. For instance, and without limitation, digestive biomarker 108 may include one or more blood samples, biopsies, prior diagnoses of digestive disease, or tests results relating to a user as described herein.

Still referring to FIG. 6, at step 610, computing device 104 generates at least a digestive parameter 112 of a plurality of digestive parameters 112 as a function of the digestive biomarker 108. Digestive parameter 112 may be any digestive parameter as described herein.

Still referring to FIG. 6, at step 615, computing device 104 determines a digestive profile 116 as a function of the at least a digestive parameter 112. The digestive profile 116 includes a numerical digestive health score 120 correlated to at least a digestive parameter 112. Digestive profile 116 includes an absorption condition 124 correlated to the at least a digestive parameter 112. Digestive parameter 112 may be any digestive parameter 112 as described herein. Digestive health score 120 may be any digestive health score 120 as described herein. Absorption condition 124 may be any absorption condition 124 as described herein. Absorption condition 124 may be correlated to increased intestinal permeability. Absorption condition 124 may be correlated to decreased intestinal permeability.

Still referring to FIG. 6, at step 620, computing device 104 identifies at least a nutrition element 128 as a function of the digestive profile 116. Nutrition element 128 may be any nutrition element 128 as described herein. Identifying at least a nutrition element 128 includes obtaining at least a nutrient composition 132 correlated to at least a nutrition element 128. Nutrient composition 132 may be any nutrient composition 132 as described herein. Identifying at least a nutrition element 128 includes determining a nourishment score 136 as a function of the effect of the nutrition element 128 on the digestive profile 116. Nourishment score 136 may be any nourishment score 136 as described herein. Determining nourishment score 136 includes generating training data using the plurality of nutrition elements 128 identified according to the digestive disease category. Training data may be any training data as described herein. Digestive disease category may be any digestive disease category as described herein. Training a nutrition element machine-learning model 140 according to the training data, wherein training data includes a plurality of data entries that correlates the nourishment score 136 for each digestive disease category to nutrient composition 132. Computing device 104 determines nutrition score 136 as a function of the nutrition element machine-learning model 140 and digestive profile 116. Computing device 104 includes identifying a nutrition element 128 as a function of the nutrient composition 132, nourishment score 136 and nutrition element machine-learning model 140. Identifying nutrition elements 128 may include classifying the digestive profile 116 to a digestive disease category and identifying the plurality of nutrition elements 128 according to the digestive disease category. The digestive disease profile 116 includes quantitative digestive health score 120 related to the at least a digestive parameter 112 and absorption condition 124 related to the at least a digestive parameter 112. Identifying the plurality of nutrition elements 128 may include identifying nutrition elements 128 intended to prevent digestive disease according to the digestive disease category. Identifying the plurality of nutrition elements 128 may include identifying nutrition elements 128 that have a positive impact on the absorption condition 124. Absorption condition 124 may be any absorption condition as described herein. Identifying the plurality of nutrition elements 128 may include identifying nutrition elements 128 that have a negative impact on the absorption condition 124.

Still referring to FIG. 6, at step 625, computing device 104 generates digestive disease nourishment program 144 as a function of the digestive profile 116, which includes digestive health score 120 and absorption condition 124. Generating the digestive disease nourishment program 144 includes training the nourishment classifier as a function of a classification machine-learning and a training set relating nutrient composition 132 and nourishment score 136 to nutrition elements 128 and outputting the nourishment program classifier as a function of the nourishment program classifier, nutrition elements, nutrient composition, and nourishment score. Nourishment classifier may be any nourishment classifier as described herein. Generating the digestive disease nourishment program 144 includes generating an adherence score. An "adherence score", for the purposes of this disclosure, is a quantitative value that reflects the level of user participation in the digestive nourishment program 144. Adherence score may be any adherence score as described herein. Generating adherence score includes calculating a change in digestive health score 120. Generating the digestive disease nourishment program 144 may include receiving at least a user preference regarding the at least a nutrition element. The user preference may be any user preference as described herein. The user preference increases the adherence score. Generating adherence score may include modifying at least a nutrition element as a function of the at least a user preference. Modification may be any modification as described herein.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 7:
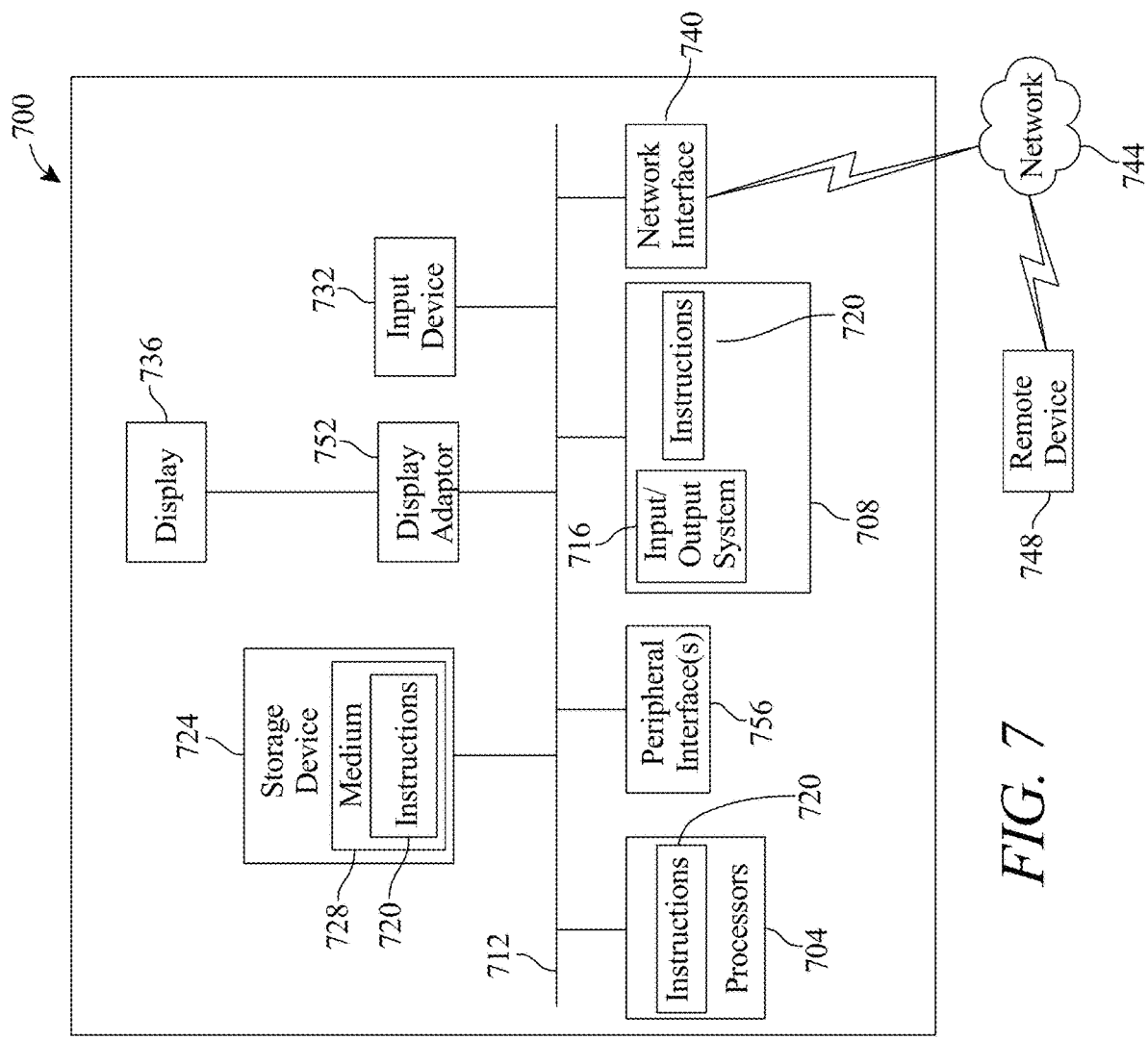
FIG. 7 is a block diagram of a computing system that can be used to implement any one or more of the methodologies disclosed herein and any one or more portions thereof.

FIG. 7 shows a diagrammatic representation of one embodiment of a computing device in the exemplary form of a computer system 700 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 700 includes a processor 704 and a memory 708 that communicate with each other, and with other components, via a bus 712. Bus 712 may include any of several types of bus structures including, but not limited to, a memory bus, a memory controller, a peripheral bus, a local bus, and any combinations thereof, using any of a variety of bus architectures.

Processor 704 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 704 may be organized according to Von Neumann and/or Harvard architecture as a non-limiting example. Processor 704 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 708 may include various components (e.g., machine-readable media) including, but not limited to, a random-access memory component, a read only component, and any combinations thereof. In one example, a basic input/output system 716 (BIOS), including basic routines that help to transfer information between elements within computer system 700, such as during start-up, may be stored in memory 708. Memory 708 may also include (e.g., stored on one or more machine-readable media) instructions (e.g., software) 720 embodying any one or more of the aspects and/or methodologies of the present disclosure. In another example, memory 708 may further include any number of program modules including, but not limited to, an operating system, one or more application programs, other program modules, program data, and any combinations thereof.

Computer system 700 may also include a storage device 724. Examples of a storage device (e.g., storage device 724) include, but are not limited to, a hard disk drive, a magnetic disk drive, an optical disc drive in combination with an optical medium, a solid-state memory device, and any combinations thereof. Storage device 724 may be connected to bus 712 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 724 (or one or more components thereof) may be removably interfaced with computer system 700 (e.g., via an external port connector (not shown)). Particularly, storage device 724 and an associated machine-readable medium 728 may provide nonvolatile and/or volatile storage of machine-readable instructions, data structures, program modules, and/or other data for computer system 700. In one example, software 720 may reside, completely or partially, within machine-readable medium 728. In another example, software 720 may reside, completely or partially, within processor 704.

Computer system 700 may also include an input device 732. In one example, a user of computer system 700 may enter commands and/or other information into computer system 700 via input device 732. Examples of an input device 732 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 732 may be interfaced to bus 712 via any of a variety of interfaces (not shown) including, but not limited to, a serial interface, a parallel interface, a game port, a USB interface, a FIREWIRE interface, a direct interface to bus 712, and any combinations thereof. Input device 732 may include a touch screen interface that may be a part of or separate from display 736, discussed further below. Input device 732 may be utilized as a user selection device for selecting one or more graphical representations in a graphical interface as described above.

A user may also input commands and/or other information to computer system 700 via storage device 724 (e.g., a removable disk drive, a flash drive, etc.) and/or network interface device 740. A network interface device, such as network interface device 740, may be utilized for connecting computer system 700 to one or more of a variety of networks, such as network 744, and one or more remote devices 748 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 744, may employ a wired and/or a wireless mode of communication. In general, any network topology may be used. Information (e.g., data, software 720, etc.) may be communicated to and/or from computer system 700 via network interface device 740.

Computer system 700 may further include a video display adapter 752 for communicating a displayable image to a display device, such as display device 736. Examples of a display device include, but are not limited to, a liquid crystal display (LCD), a cathode ray tube (CRT), a plasma display, a light emitting diode (LED) display, and any combinations thereof. Display adapter 752 and display device 736 may be utilized in combination with processor 704 to provide graphical representations of aspects of the present disclosure. In addition to a display device, computer system 700 may include one or more other peripheral output devices including, but not limited to, an audio speaker, a printer, and any combinations thereof. Such peripheral output devices may be connected to bus 712 via a peripheral interface 756. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for generating a digestive disease nourishment program, the system comprising: a computing device, the computing device configured to:

receive at least a digestive biomarker relating to a user;
generate at least a digestive parameter as a function of the at least a digestive disease biomarker;
determine a digestive profile as a function of the at least a digestive parameter;
identify at least a nutrition element as a function of the digestive profile, wherein identifying comprises:
  determining, for each nutrition element of a plurality of nutrition elements, a nourishment score as a function of the effect of the nutrition element on the digestive profile;
  generating training data as a function of the plurality of nutrition elements, wherein the training data correlates each nourishment score to a nutrient composition for each nutritional element of the plurality of nutrition elements;
  training a machine-learning model as a function of a machine-learning process and the training data;
  identifying a first nutrient composition as a function of the machine-learning model;
  receiving a nourishment training set correlating nutrition elements to nutrient compositions;
  training a classification machine-learning process as a function of the nourishment training set; and
  classifying the at least a nutrition element to a class including the first nutrient composition as a function of the classification machine-learning process and the first nutrient composition; and
generate a digestive disease nourishment program as a function of the nutrition element and the digestive profile.

2. The system of claim 1, wherein receiving the at least the digestive biomarker comprises receiving a result of one or more tests relating the user.

3. The system of claim 1, wherein receiving the at least the digestive biomarker comprises receiving a prior diagnosis of a digestive disease relating to the user.

4. The system of claim 1, wherein identifying the at least a nutrition element comprises:
  classifying the digestive profile to a digestive disease category, wherein:
    the digestive profile includes a quantitative digestive health score correlated to the at least a digestive parameter; and
    the digestive profile includes an absorption condition correlated to the at least a digestive parameter; and
  identifying the at least a nutrition element according to the digestive disease category.

5. The system of claim 4, wherein identifying the at least a nutrition element further comprises identifying at least a nutrition element intended to prevent digestive disease according to the digestive disease category.

6. The system of claim 1, wherein generating the digestive disease nourishment program comprises:
  receiving at least a user preference regarding the at least a nutrition element; and
  modifying the at least a nutrition element as a function of the at least a user preference.

7. The system of claim 1, wherein identifying the nutrition elements comprises identifying nutrition elements that have a positive impact on an absorption condition.

8. The system of claim 7, wherein the absorption condition is correlated to increased intestinal permeability.

9. A method for generating a digestive disease nourishment program, the method comprising:
receiving at least a digestive biomarker relating to a user;
generating at least a digestive parameter of a plurality of digestive parameters as a function of the digestive disease biomarker;
determining a digestive profile as a function of the at least a digestive parameter;
identifying at least a nutrition element as a function of the digestive profile, wherein identifying comprises:
  determining, for each nutrition element of a plurality of nutrition elements, a nourishment score as a function of the effect of the nutrition element on the digestive profile;
  generating training data as a function of the plurality of nutrition elements, wherein the training data correlates each nourishment score to a nutrient composition for each nutritional element of the plurality of nutrition elements;
  training a machine-learning model as a function of a machine-learning process and the training data;
  identifying a first nutrient composition as a function of the machine-learning model;
  receiving a nourishment training set correlating nutrition elements to nutrient compositions;
  training a classification machine-learning process as a function of the nourishment training set;
  classifying the at least a nutrition element to a class including the first nutrient composition as a function of the classification machine-learning process and the first nutrient composition; and
generating a digestive disease nourishment program as a function of the nutrition element and the digestive profile.

10. The method of claim 9, wherein receiving at least the digestive biomarker comprises receiving a result of one or more tests relating the user.

11. The method of claim 9, wherein receiving at least the digestive biomarker comprises receiving a prior diagnosis of a digestive disease relating to the user.

12. The method of claim 9, wherein identifying the at least a nutrition element comprises:
  classifying the digestive profile to a digestive disease category, wherein:
    the digestive profile includes a quantitative digestive health score correlated to the at least a digestive parameter; and
    the digestive profile includes an absorption condition correlated to the at least a digestive parameter; and
  identifying the at least a nutrition element according to the digestive disease category.

13. The method of claim 12, wherein identifying the at least a nutrition element comprises identifying at least a nutrition element intended to prevent digestive disease according to the digestive disease category.

14. The method of claim 9, wherein generating the digestive disease nourishment program comprises:
  receiving at least a user preference regarding the at least a nutrition element; and
  modifying the at least a nutrition element as a function of the at least a user preference.

15. The method of claim 9, wherein identifying the nutrition elements comprises identifying nutrition elements that have a positive impact on an absorption condition.

16. The method of claim 15, wherein the absorption condition is correlated to increased intestinal permeability.

* * * * *